United States Patent [19]

Michalak

[11] 4,335,606

[45] Jun. 22, 1982

[54] APPARATUS AND METHOD FOR MEASURING FLUID

[76] Inventor: Janusz K. Michalak, 10 Hunter La., Elmsford, N.Y. 10523

[21] Appl. No.: 159,358

[22] Filed: Jun. 13, 1980

[51] Int. Cl.$^3$ .......................................... G01F 23/04
[52] U.S. Cl. .............................. 73/298; 33/126.7 R; 73/323
[58] Field of Search ...................... 73/298; 33/126.7 R

[56] References Cited

U.S. PATENT DOCUMENTS

| 1,501,407 | 7/1924 | Le Clair | 33/126.7 R |
| 2,451,704 | 10/1948 | Wood | 73/298 X |
| 2,660,058 | 11/1953 | Vogt | 73/290 R |
| 3,055,217 | 9/1962 | Vogt | 73/298 |
| 3,662,470 | 5/1972 | Sasgen | 33/126.7 R |

Primary Examiner—Daniel M. Yasich
Attorney, Agent, or Firm—Jenkins, Coffey, Hyland, Badger & Conard

[57] ABSTRACT

An apparatus for measuring the level of at least one fluid includes an elongated transparent tubular member open at both ends, one of the ends being vertically insertable into the fluid to a reference point below the fluid surface to establish a column of the fluid in the tubular member having a length generally equal to the distance between the reference point and the fluid surface, a stiff tether slightly longer in length than the tubular member and threaded therethrough, a plug connected to one end of the tether for closing at least the inserted end of the tubular member prior to withdrawing it from the fluid to contain the column of the fluid in the tubular member for measurement after the tubular member is withdrawn from the fluid, and a grip connected to the other end of the cable for remotely controlling the plug to close the inserted end of the tubular member. In the process of measuring the fluid level, the column of the fluid can be viewed through the tubular member to check for abnormalities in the fluid and the presence or absence of other immiscible fluids.

10 Claims, 4 Drawing Figures

APPARATUS AND METHOD FOR MEASURING FLUID

The present invention relates generally to devices for measuring fluids. More particularly, the present invention relates to an apparatus and method of fluid measurement which is adapted for measuring the fluid from a location remote to the fluid surface by withdrawing a sample of the fluid and observing the withdrawn sample. For example, the apparatus and method of the present invention may be advantageously used to remotely measure the ground water level from the ground surface of measure fluid levels in submerged storage tanks.

The importance of monitoring the ground water level to the determination of infiltration of foreign material in sewer pipes is well known to those concerned with designing and maintaining sewer systems. Both the level and chemical characteristics of the ground water influence the infiltration of foreign material into sewer systems, and it has been found that the degree of infiltration is directly related to the level of the ground water above the sewer pipes. Because of this influence of the ground water on infiltration, continuous monitoring of the ground water level is necessary in order to regularly evaluate and analyze the infiltration problem. Heretofore, regular monitoring of the ground water level in the field has been accomplished by one or more of the following apparatus and methods: (1) by observing ground water gauges permanently installed in sewer manholes at an elevation near the top of the lowest sewer pipe passing through the manhole; (2) by observing ground water gauges installed adjacent to the sewer pipes and/or manholes; (3) by observing the water levels in existing ground water wells; and (4) by observing the water levels in specially dug ground water wells.

In a typical ground water gauge installation in a sewer manhole, the gauge includes a pipe inserted through the wall of the manhole at an elevation near the top of the lowest sewer pipe and a transparent plastic viewing tube with a calibrated scale permanently attached to this pipe so that a column of water in the transparent viewing tube represents the ground water level outside the sewer manhole. This gauge installation makes it necessary for an individual to climb down into the sewer manhole in order to measure the ground water level. For safety reasons, each time an individual enters the sewer manhole, the manhole must first be cleared of any gases which may be present. The process of clearing the gases and blocking off an area in proximity to the manhole for the purpose of gathering information related to the ground water level is an inefficient utilization of both time and manpower.

In a typical installation of a ground water gauge adjacent to the sewer pipes or manhole, the ground water level is typically measured by inserting a stick into a well casing and measuring the length of the unwetted portion of the stick after retrieval from the well. This apparatus and method of measuring the ground water level is many times unreliable because it involves an indirect gauging of the ground water level. Accordingly, such variables as the stiffness of the stick, the length of the stick, or the physical characteristics of the measured liquid, such as its viscosity, can influence the accuracy of the measurement made by this conventional apparatus and method.

In another application of devices for measuring fluids, the fluid level in a submerged storage tank is typically measured by the dip stick method described above. Many times it may be desirable to also determine whether other immiscible fluids are present or absent in the storage tank. For example, it would be desirable to know how much, if any, water is present in a gasoline storage tank, or it may be desirable to know the thickness of a hydrocarbon fluid spill on a water surface. Heretofore, conventional apparatus and methods for measuring fluids have been incapable of providing this type of information.

It is therefore one object of the present invention to provide a method of measuring the level of a fluid by vertically inserting one end of an elongated transparent tubular member into the fluid to a reference point below the fluid surface, closing the one end of the tubular member located below the fluid surface from a remote location to contain a column of the fluid in the tubular member prior to withdrawing it from the fluid, withdrawing the tubular member from the fluid, and measuring the column of fluid contained in the tubular member after it is withdrawn.

It is a further object of the present invention to provide an apparatus for measuring the level of ground water beneath the ground surface which allows an individual to make the measurement from the ground surface in accordance with the method described above. Accordingly, a measurement of the ground water level above the pipes in a sewer system can be made by an individual in a sewer manhole measuring installation from the ground surface without entering the sewer manhole.

According to the present invention, an apparatus for measuring the level of a fluid includes an elongated transparent tubular member having both of its ends open, one of the ends being vertically insertable into the fluid to a reference point below the fluid surface to establish a column of the fluid in the tubular member having a length generally equal to the distance between the reference point and the fluid surface, a stiff tether having a length slightly greater than the tubular member and threaded therethrough, a plug connected to one end of the tether for closing at least the inserted end of the tubular member prior to withdrawing it from the fluid, and a grip remotely connected to the other end of the cable for controlling the plug to close the inserted end of the tublar member and contain the column of the fluid therein prior to withdrawing it from the liquid.

Further according to the present invention, the apparatus and method described above can be advantageously used for measuring the levels and relationships of two or more immiscible fluids by viewing the sample of the fluids through the tubular member after it is withdrawn.

Various other features and advantages of the present invention will become apparent in view of the following detailed description of one embodiment thereof, which description should be considered in conjunction with the accompanying drawings, in which.

In a typical ground water level measurement installation for monitoring the ground water level above the pipes in a sewer system, a monitoring tube is installed in a sewer manhole at an elevation near the top of the lowest sewer pipe in the manhole. The tube is transparent and connected to the ground water outside the manhole so that the monitoring tube is filled with a column of the fluid which represents the ground water level outside the manhole. In this typical ground water level measurement installation, it is therefore necessary for an individual to enter the manhole in order to observe and measure the height of the column in the monitoring tube to determine the ground water level above the pipes in the sewer system. This typical ground water level measurement installation involves inefficient use of both time and manpower in order to continuously and regularly obtain needed information related to the ground water level. One individual using the present invention can quickly and accurately measure the ground water level from the ground surface without ever entering the sewer manhole. Therefore, the apparatus and method according to the present invention greatly increases the efficiency of measuring the ground water level.

While the present invention may be advantageously used for making regular measurements of the ground water level above pipes in a sewer system, and for illustrative purposes is described herein in association with the measurement of the ground water level outside a sewer manhole, it will be understood that the apparatus and method of the present invention may also be advantageously used in other applications for accurately and efficiently measuring the level of one or more fluids where the fluid surface is not easily accesible, for example, where the fluid is contained in a submerged storage tank. Accordingly, it is not intended that the present invention be limited to the application described hereinafter.

Figure 1:
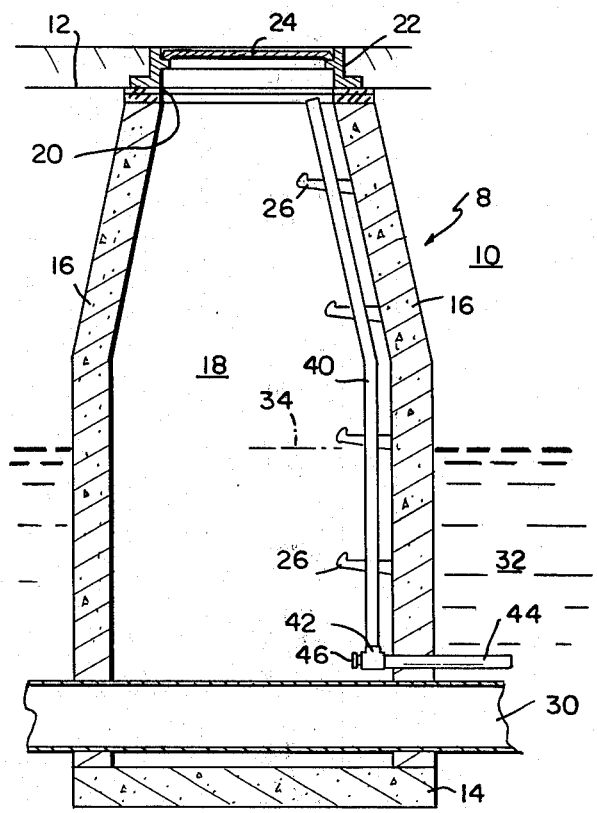
FIG. 1 is a cross-sectional view of a conventional sewer manhole including a liquid-level measurement installation employing the apparatus and method according to the present invention.

Shown in FIG. 1 is a conventional sewer manhole 8 located in the ground 10 and submerged beneath the ground surface 12. This manhole 8 has a base or floor 14 and an upwardly extending generally cylindrical side wall 16 forming a partially enclosed chamber 18 beneath the ground surface 12. The side walls 16 are tapered in proximity to toward the ground surface 12 and terminate to provide an opening 20 at the ground surface 12 which allows access to the chamber 18. Typically, the opening 20 is closed at the ground surface 12 by a cover structure 22 which includes a removable lid 24 to allow entry into the manhole 8. Connected to the side wall 16 is a series of steps 26 to assist an individual in entering and exiting the manhole 8.

Passing through the manhole 8 in proximity to the base or floor 14 is a sewer pipe 30. Typically, ground water 32 outside of the manhole 8 has a level 34 (represented by the dotted line) which is above the sewer pipe 30 and which therefore covers the sewer pipe 30 outside the manhole 8. It is well known that both the level and chemical characteristics of the ground water 32 have an influence on the infiltration into the sewer system of foreign matter from the ground 10. Furthermore, the degree of infiltration has been shown to be directly related to the level of the ground water 32 above the sewer pipe 30. Accordingly, it is desirable that the ground water level 34 be continuously monitored to regularly analyze and evaluate the effect of the ground water 32 on the sewer system.

Figure 2:
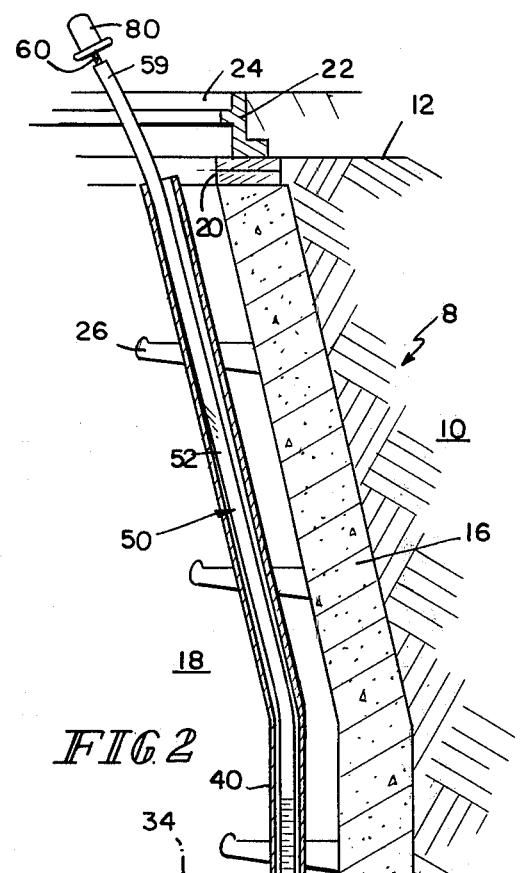
FIG. 2 is an enlarged sectional view of the manhole and installation shown in FIG. 1 illustrating the method of measuring the liquid level using the apparatus of the present invention.
Figure 3:
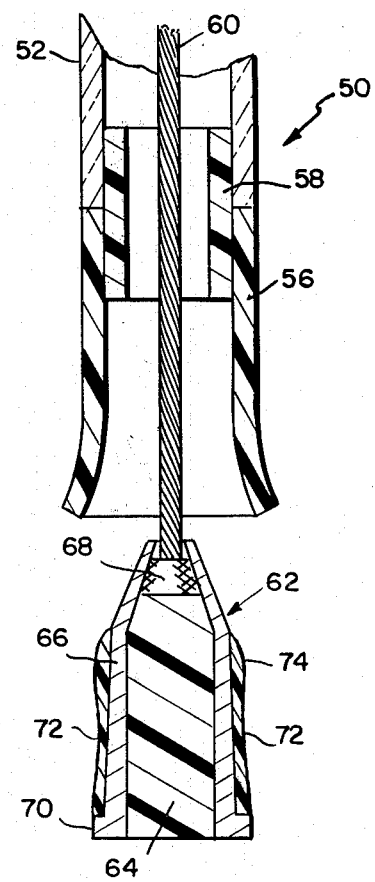
FIG. 3 is a fragmentary view, partly cross-sectioned, of the liquid-level measuring apparatus shown in FIG. 2.

A ground water level measurement installation according to the present invention eliminates the need for an individual to enter the manhole 8 in order to regularly gather information related to the ground water level 34 outside the manhole 8. Referring now to FIGS. 1, 2, and 3, the ground water level measurement apparatus of the present invention includes an elongated and generally vertical hollow liquid level monitoring pipe or shaft 40 which is secured to the steps 26 of the manhole 8 and extends from an elevation near the top of the lowest sewer pipe 30 passing through the manhole 8 to the opening 20 of the manhole 8 at the ground surface 12. This elongated hollow monitoring pipe 40 is permanently installed in the manhole 8 and connected by a T-shaped pipe coupling 42 to a generally horizontal liquid inlet pipe 44 which is inserted through the side wall 16 of the manhole 8 to provide a passageway between the ground water 32 and the monitoring pipe 40. This liquid inlet pipe 44 is located as close as possible to the top of the lowest sewer pipe 30 so that it establishes a point of reference in proximity to the sewer pipe 30 for measuring the ground water level 34 above the sewer pipe 30. A removable plug 46 may be provided in the T-shaped pipe coupling 42 for purposes of gaining access to the liquid inlet pipe 44 for cleaning.

In accordance with well-known principles of physics and fluid mechanics, the ground water 32 flows through the liquid inlet pipe 44 and establishes a column of the ground water 32 in the monitoring pipe 40 which has a height equal to the distance between the ground water surface and the inlet pipe 44 or reference point. Since both the ground water surface and the column of ground water in the monitoring pipe 40 are exposed to the atmosphere above the ground surface 12, the pressure on each is generally the same so that the column of ground water will have a height generally equal to the ground water level 34. This relationship generally obeys the principles of hydrostatic equilibrium. The column of the ground water 32 is therefore an accurate and direct representation of the ground water level 34 above the sewer pipe 30.

Referring now more particularly to FIGS. 2 and 3, a gauge for sampling and measuring the ground water level 34 is insertable into the monitoring pipe 40 to the depth of the liquid inlet pipe 44 (reference point) located beneath the ground water surface, and a column of the ground water 32 is withdrawn from the monitoring pipe 40 which represents the ground water level 34 above the sewer pipe 30. The gauge includes an elongated transparent hollow tubular member 50 having a relatively small diameter which is insertable through the monitoring pipe 40 into the ground water 32 in the monitoring pipe 40. The monitoring pipe 40 therefore also serves as a channel or guide for vertically positioning the elongated tubular member 50 into the ground water 32 provided therein. It will be understood that the length of the elongated tubular member 50 will be determined by the distance between the ground water surface and the reference point from which the measurement is being made.

In the illustrative embodiment, the elongated tubular member 50 includes a flexible transparent section 52 formed from material, such as a clear plastic, which allows the tubular member 50 to be rolled up for storage when not in use or carried from manhole to manhole for making a plurality of measurements. A series of calibrations 54 may be provided on the flexible transparent section 52 of the tubular member 50 to provide a quick determination of the ground water level 34 after the tubular member 50 is withdrawn from the monitoring tube. Although not shown, a sliding marker may also be provided on the flexible transparent section 52 to gauge the ground water level 34. The tubular member 50 also includes a flared end section 56 constructed of a soft pliable PVC material or rubber. The end section 56 of the tubular member 50 is flared outwardly and is connected to the flexible transparent section 52 by an inner connecting sleeve 58.

Both ends 56, 59 of the elongated tubular member 50 are open for receiving a relatively stiff tether 60 such as a steel cable which is threaded through the tubular member 50. The tether 60 has a length slightly greater than the length of the tubular member 50 so that ends of the tether 60 extend beyond the ends 56, 59 of the tubular member 50. Connected to one end of the tether 60 in proximity to the flared end section 56 of the tubular member 50 is a plug 62. As best shown in FIG. 3, the plug 62 includes a body 64 formed of a sealant material which is encased within a cylindrical inwardly tapering metallic side wall 66. Retained by the inwardly tapered side wall 66 of the plug 62 is a clamp 68 for connecting the plug 62 to the tether 60. Formed around the periphery of the plug 62 at its distal end from the tether connection 68 is a flange 70 which provides a ledge for supporting a sleeve or coating of soft PVC material 72 or rubber. In proximity to the cable connection 68, the soft material coating 72 bulges to form a protuberant curb 74 around the periphery of the plug 62 for locking the plug 62 in the flared end section 56 of the tubular member 50.

The shape and material of the plug 62 and the end section 56 of the tubular member 50 have been selected so that when the plug 62 is forced upward to close the opening in the end section 56, it becomes wedged in a locked position within the end section 56 of the tubular member 50 due to the friction between the PVC materials of the plug 62 and end section 56. Therefore, even when the force on the plug 62 is removed, it remains lodged in the opening of the end section 56.

Remotely connected on the other end of the tether 60 in proximity to the end 59 of the tubular member 50 is a handle or grip 80 which, when pulled, applies a force to seat and lock the plug 62 within the opening of the end section 56 of the tubular member 50, thereby closing the end section 56 thereof. Furthermore, the handle or grip 80 may be pushed to apply a force on the stiff tether 60 to release the engagement of the plug 62 with the end section 56 and thereby open the end section 56 of the tubular member 50.

The length and material of the tether 60 have been selected so that when the handle or grip 80 is pushed to thereby fully extend the tether 60 beyond the end section 56 of the tubular member 50, the tether functions like a stiff spring in relation to the plug 62 to prevent the plug 62 from unintentionally being forced into engagement with the end section 56 of the tubular member 50, and thereby accidentally closing the end section 56 thereof. This feature is particularly important where the tubular member 50 must be inserted into a monitoring pipe 40 having one or more bends.

In operation, the elongated tubular member 50 is inserted into the monitoring pipe 40 until it bottoms on the liquid-inlet pipe 44 which represents the reference point location from which the measurement of the ground water level 34 is to be taken. As the tubular member 50 is inserted into the ground water 32 in the monitoring pipe 40, the end section 56 is prevented from unintentionally closing by applying a pushing force to the handle or grip 80, and the tubular member is filled with a column of the ground water 32. Once the column of the ground water 32 is established in the tubular member 50 and before the tubular member 50 is withdrawn from the monitoring pipe 40, the remote grip 50 is pulled to force the plug 62 to engage the flared end section 56 of the tubular member 50 and thereby close the end section 56 to contain the column of ground water 32 in the tubular member 50. Thereafter, the tubular member 50 is withdrawn from the monitoring pipe 40 with the column of ground water 32 contained therein and the ground water level 34 is accurately represented by the height of the column of ground water 32 in the tubular member 50. The ground water level 34 is measured by the series of calibrations 54 provided on the transparent section 52 of the tubular member 50. Once the measurement has been made, the plug 62 can be removed from the flared end section 56 to allow the column of ground water 32 to flow out of the tubular member 50 and the gauge is therefore cleared for use in making further measurements.

Figure 4:
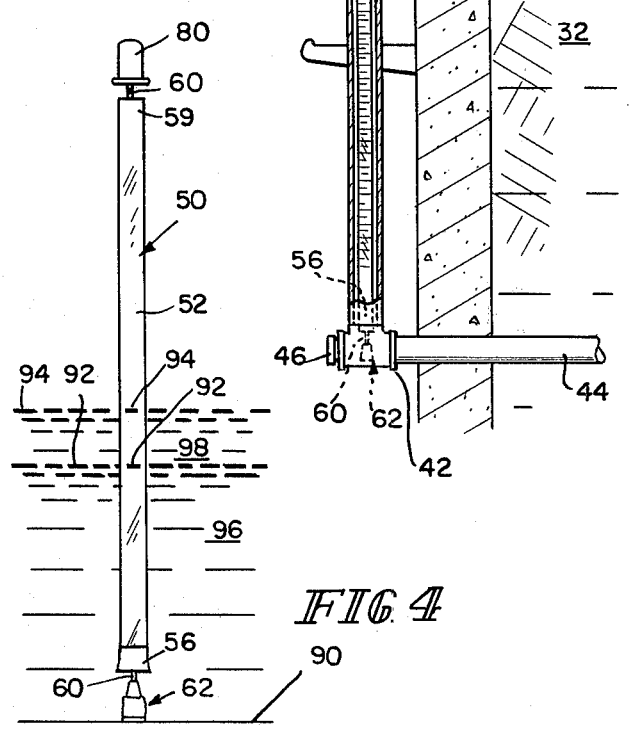
FIG. 4 is a diagrammatic representation of the use of the apparatus shown in FIGS. 2 and 3 for measuring the levels of two or more immiscible fluids.

Referring now to FIG. 4, another application for the apparatus and method of the present invention is diagrammatically illustrated. In a fluid storage tank (not shown) or other means for containing a fluid having a bottom 90 (reference point location), it may be desirable to measure the levels 92, 94 of two or more immiscible fluids 96, 98, respectively. For example, in a gasoline storage tank submerged beneath the ground surface, it would be desirable to know not only the level of the gasoline in the tank but also the level of any water in the tank. According to the present invention, the transparent tubular member 50 can be inserted into the fluids 96, 98 to the bottom 90 which represents the reference point location for measuring the fluids and a sample column of the fluids 96, 98 withdrawn, which accurately and directly represents the levels 92, 94 and relationship of the fluids 96, 98, respectively. Since the tubular member 50 is transparent, the relationship of the fluids can be observed after the tubular member 50 is withdrawn.

It should further be noted that the plug 62 may be forced into engagement with the tubular member 50 to close the end section 56 by first resting the plug 62 on the bottom 90 of the container for the fluids, and then forcing the tubular member 50 downward to seat the plug 62 in the end section 56. In this embodiment, the grip 80 may be eliminated and the tether 60 may be movably retained within the tubular member 50 to support the plug 62.

What is claimed is:
1. An apparatus for measuring the level of a fluid from a remote location, comprising means providing a reference point below the fluid surface, an elongated hollow shaft providing a permanent passageway from the remote location to the reference point, and an elongated transparent tubular member having both of its ends open, a first end of the tubular member being insertable through the shaft into the fluid to the reference point below the fluid surface to establish a column of the fluid in the tubular member having a height generally equal to the level of the fluid above the reference point, the tubular member including a relatively stiff tether threaded therethrough and extending beyond the ends thereof, a plug connected to the tether in proximity to the first end of the tubular member for closing the first end prior to withdrawing the tubular member from the shaft to contain the column of the fluid therein, the first end of the tubular member including an outwardly flared section of pliable material for receiving the plug, the plug being tapered for entering the flared section of the first end of the tubular member, the plug including a sleeve of pliable material for frictionally engaging the flared section of pliable material of the first end to lock the plug in the first end, and means connected to the tether in proximity to a second end of the tubular member for applying a force sufficient to seat the plug in a locked position in the first end.

2. An apparatus for measuring the levels of two or more immiscible fluids, comprising a transparent tubular member having two open ends, one of the ends being insertable into the fluids to a desired reference point to establish a column of the immiscible fluids in the tubular member, each immiscible fluid in the column having a height generally equal to the level of its surface above the reference point, and means for closing at least the one end of the tubular member prior to withdrawing it from the fluids to contain the column of fluids in the tubular member in their immiscible relationship for observation through the tubular member when it is withdrawn from fluids, the closing means including a tether extending through the tubular member and having first and second ends in proximity to the open ends of the tubular member, means connected to the first end of the tether for engaging the one end of the tubular member, the one end of the tubular member including an outwardly flared section of pliable material for receiving the engaging means, the engaging means being tapered to enter the flared section, the engaging means including a section of pliable material for frictionally engaging the section of pliable material of the one end to lock the engaging means in the one end, and means connected to the second end of the tether for applying a force sufficient to seat the engaging means in a locked position in the flared section before withdrawing the tubular member from the fluids to contain the column of fluids therein.

3. An apparatus for measuring the level of a fluid, comprising a transparent tubular member having first and second open ends, the first end being insertable into the fluid to a reference point below the fluid surface to establish a column of the fluid in the tubular member having a length generally equal to the distance between the reference point and the surface of the fluid, a tether passing through the tubular member, the tether including first and second ends and having a length slightly greater than the length of the tubular member so that the first end of the tether extends beyond the first end of the tubular member, a plug connected to the first end of the tether, the first end of the tubular member including an outwardly flared section of pliable material for receiving the plug, the plug being tapered for entering the flared section of the first end of the tubular member, the plug including means for frictionally engaging the pliable material to lock the plug in the first end, and means connected to the second end of the tether for applying a force sufficient to seat the plug in locking engagement with the flared section to close the first end of the tubular member and contain the column of fluid therein prior to withdrawal of the tubular member from the fluid.

4. The apparatus as recited in claim 3, wherein the plug includes a sleeve of pliable material for engaging the flared section of pliable material of the tubular member to secure the plug in the first end thereof.

5. The apparatus as recited in claim 4 wherein the sleeve of pliable material on the plug includes a protuberant portion for locking the plug in the flared section of the tubular member.

6. The apparatus as recited in claim 3 wherein the tether extends through the tubular member and the second end of the tether extends beyond the second end of the tubular member for remotely controlling the movement of the plug.

7. The apparatus as recited in claim 6, wherein the means connected to the second end of the tether includes a grip to pull the plug into engagement with the first end of the tubular member.

8. The apparatus as recited in claim 7 wherein the tether is a stiff cable.

9. The apparatus as recited in claim 3 wherein the tubular member is flexible and includes a series of calibrations for determining the level of the fluid relative to the reference point after the tubular member is withdrawn from the fluid.

10. In a method of measuring the level of ground water covering a submerged sewer system which includes the steps of channeling the ground water into a monitoring pipe located in a sewer manhold wherein the level of the water in the pipe represents the level of the ground water above the sewer system and measuring the level of the ground water in the pipe, the improvement comprising the steps of removing a column of the ground water from the monitoring pipe having a height generally equal to the distance between the ground water surface and means providing a reference point slightly above the sewer system by inserting at least one end of an open-ended transparent tubular member into the monitoring pipe to the reference point; prior to withdrawing the tubular member from the monitoring pipe, containing the column of ground water in the tubular member by applying a force at the other end of the tubular member to a tether coupled to a plug at the one end of the tubular member to draw the plug into the one end; locking the plug in the one end of the tubular member so that the column of water is contained without maintaining the force; withdrawing the tubular member from the monitoring pipe; and measuring the height of the contained column of water through the transparent tubular member.

* * * * *